US010972200B2

(12) United States Patent
Kubo et al.

(10) Patent No.: US 10,972,200 B2
(45) Date of Patent: Apr. 6, 2021

(54) DATA RECEIVING APPARATUS AND DATA TRANSMITTING APPARATUS

(71) Applicants: OMRON HEALTHCARE CO., LTD., Muko (JP); OMRON Corporation, Kyoto (JP)

(72) Inventors: Nobuo Kubo, Kyoto (JP); Toru Deno, Kyoto (JP); Hideki Kondo, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 0 days.

(21) Appl. No.: 16/701,297

(22) Filed: Dec. 3, 2019

(65) Prior Publication Data

US 2020/0106537 A1    Apr. 2, 2020

Related U.S. Application Data

(63) Continuation of application No. PCT/JP2018/028817, filed on Aug. 1, 2018.

(30) Foreign Application Priority Data

Aug. 9, 2017  (JP) .............................. JP2017-154757

(51) Int. Cl.
*H04B 17/318*   (2015.01)
*A61B 5/00*     (2006.01)
(Continued)

(52) U.S. Cl.
CPC ......... *H04B 17/318* (2015.01); *A61B 5/0006* (2013.01); *A61B 5/02225* (2013.01);
(Continued)

(58) Field of Classification Search
CPC .......................... H04B 17/318; H04W 52/242; H04W 52/245; A61B 5/02225; A61B 5/0006;
(Continued)

(56) References Cited

U.S. PATENT DOCUMENTS

2008/0058616 A1    3/2008   Nakagawa et al.
2010/0035334 A1    2/2010   Okuda et al.
(Continued)

FOREIGN PATENT DOCUMENTS

| JP | 2008-061663 A | 3/2008 |
| JP | 2009-198491 A | 9/2009 |
| JP | 5852620 B2    | 2/2016 |

OTHER PUBLICATIONS

Official Communication issued in International Patent Application No. PCT/JP2018/028817, dated Oct. 16, 2018.

*Primary Examiner* — Thanh C Le
(74) *Attorney, Agent, or Firm* — Keating and Bennett, LLP

(57) ABSTRACT

According to an aspect of the present invention, a data receiving apparatus includes a receiver configured to receive a one-way communication packet transmitted from a data transmitting apparatus; a calculator configured to calculate a reception signal strength of the packet at the receiver; a comparison unit configured to compare the calculated reception signal strength with a threshold value; a generation unit configured to generate assistance information relating to transmission power of the data transmitting apparatus if the reception signal strength exceeds a threshold value as a result of the comparison; and an output unit configured to output the assistance information.

3 Claims, 6 Drawing Sheets

(51) Int. Cl.
  *A61B 5/022*   (2006.01)
  *G01N 33/487*   (2006.01)
  *H04L 29/06*   (2006.01)

(52) U.S. Cl.
  CPC ... *G01N 33/48792* (2013.01); *H04L 63/0428* (2013.01); *A61B 2560/0209* (2013.01)

(58) Field of Classification Search
  CPC ...... A61B 2560/0209; G01N 33/48792; H04L 63/0428
  See application file for complete search history.

(56) References Cited

U.S. PATENT DOCUMENTS

| | | | |
|---|---|---|---|
| 2013/0137378 A1* | 5/2013 | Folden | H04W 52/245 455/67.11 |
| 2015/0036514 A1* | 2/2015 | Zhu | H04W 52/244 370/252 |
| 2016/0029149 A1 | 1/2016 | Morikawa et al. | |
| 2018/0288716 A1* | 10/2018 | Ghim | H04W 52/242 |
| 2019/0025420 A1* | 1/2019 | Frick | G01S 13/60 |
| 2019/0174506 A1* | 6/2019 | Willis, III | H04W 72/085 |

* cited by examiner

| | Public | Privata |
|---|---|---|
| Threshold | Th1 | Th2 |
F I G. 8
| | Unencrypted | Encrypted |
|---|---|---|
| Threshold | Th3 | Th4 |
F I G. 9
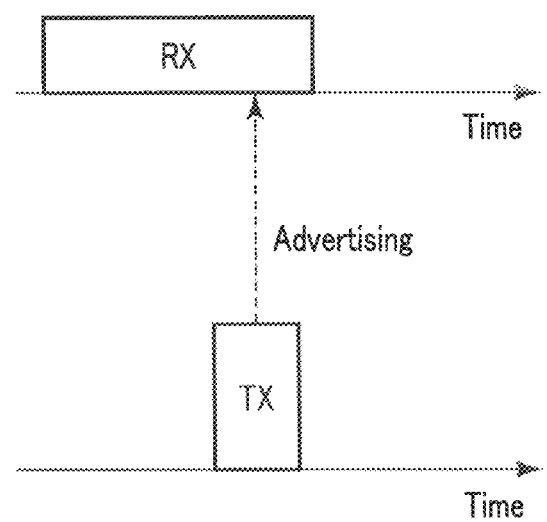
F I G. 10

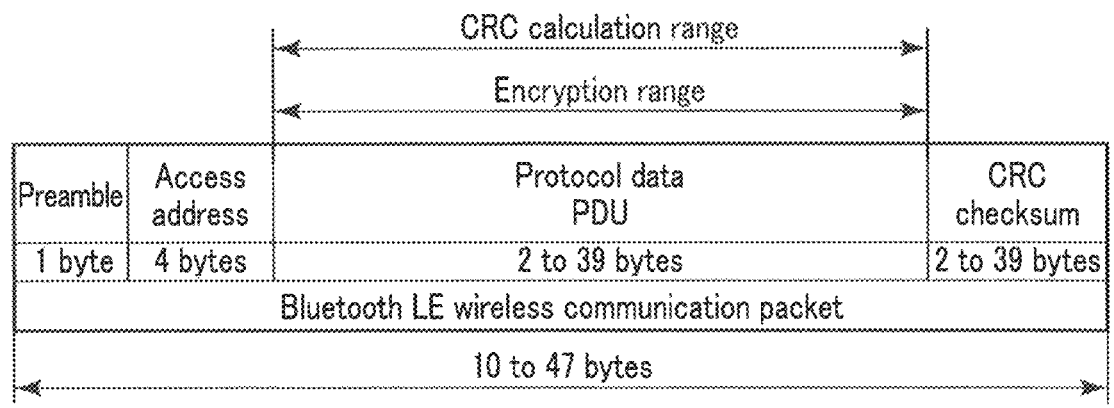
F I G. 11
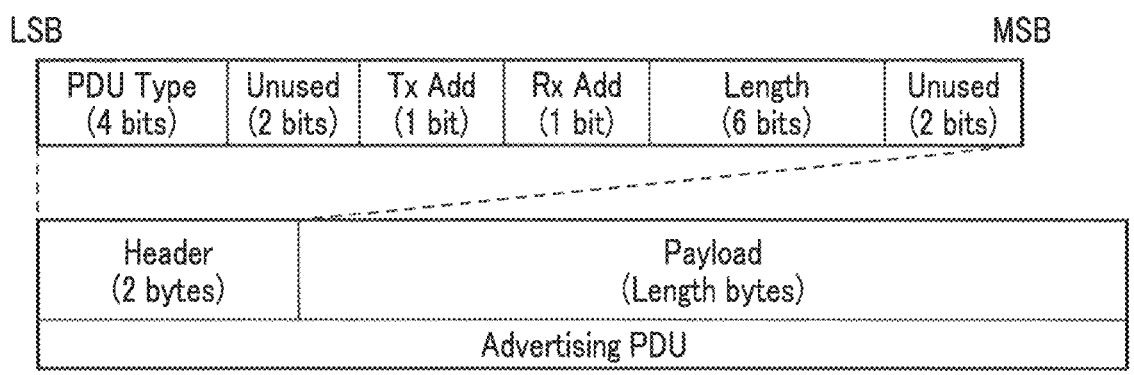
F I G. 12

DATA RECEIVING APPARATUS AND DATA TRANSMITTING APPARATUS

CROSS-REFERENCE TO RELATED APPLICATIONS

This application is a Continuation Application of PCT Application No. PCT/JP2018/028817, filed Aug. 1, 2018 and based upon and claiming the benefit of priority from Japanese Patent Application No. 2017-154757, filed Aug. 9, 2017, the entire contents of all of which are incorporated herein by reference.

FIELD

Embodiments described herein relate generally to data transmission/reception via one-way communication.

BACKGROUND

Blood pressure monitors provided with a function of transmitting blood pressure data to a user's portable information terminal have been introduced to the market. As a portable information terminal, a smartphone, a tablet terminal or a notebook personal computer may be used, for example. This function allows the user to view his/her own blood pressure measurement results under various conditions in list form on the portable information terminal. Typically, Near Field Communication technology, particularly Bluetooth (registered trademark) technology is used for transmission of the blood pressure data. In general, the Bluetooth communication (connection) can be realized on a smaller scale and in a power-saving manner in comparison to Wireless Local Area Network (WLAN) communication. The Bluetooth specification version 4.0 is also referred to as "Bluetooth Low Energy" (BLE), which can further reduce power consumption in comparison to the conventional scheme.

With BLE, a two-way communication known as "connection" can be performed. The connection, however, raises some issues. For example, the user is required to go through complicated operations for pairing; the communication procedure after the pairing is complicated; the mobile information terminal needs to support BLE; high-performance hardware (processor and memory) is required not only for the mobile information terminal but also for the blood pressure monitor; high development/evaluation costs are required; and an excessive amount of communication overhead makes the connection unsuitable for transmission of a small amount of data.

With BLE, one-way communication known as "advertising" can also be performed. Japanese Patent No. 5852620 discloses a technique of transmission with any type of data included in the margin of the data field of an advertisement packet.

The use of advertising for the transmission of the blood pressure data eliminates the need for pairing and subsequent complicated communication procedures, thereby either solving or mitigating the above-mentioned issues. However, with the blood pressure monitor provided with only a one-way transmission function, control data cannot be transmitted for control from the portable information terminal to the blood pressure monitor, and the state of the portable information terminal (such as data reception state) cannot be referred to from the blood pressure monitor side.

In general, it is possible that the data wirelessly transmitted from the blood pressure monitor may be received by any data receiving apparatus other than the user's portable information terminal, depending on the propagation of the radio wave. If the blood pressure data is transmitted without being encrypted, there is the possibility that other people may view the user's blood pressure data. Such leakage of information on the user's health condition needs to be prevented; the security of the function of transmitting the blood pressure data must be enhanced. As mentioned above, a blood pressure monitor provided with a one-way transmission function cannot refer to the data reception state of the portable information terminal. To avoid data deficit on the portable information terminal side, packets may be sent with more power than necessary. If this is the case, the likelihood of leakage of information on the user's health condition may increase.

SUMMARY

According to the first embodiment of the present invention, a data receiving apparatus includes: a receiver configured to receive a one-way communication packet transmitted from a data transmitting apparatus; a calculator configured to calculate a reception signal strength of the packet at the receiver; a comparison unit configured to compare the calculated reception signal strength with a threshold value; a generation unit configured to generate assistance information relating to an operation for lowering the transmission power of the data transmitting apparatus if the reception signal strength exceeds a threshold value, as a result of the comparison; and an output unit configured to output the generated assistance information. With such a data receiving apparatus, even if only a one-way communication transmission function is provided, the user is allowed to control the transmission power of the data transmitting apparatus to an appropriate value through use of the user input, which is made in response to assistance information. For example, when the distance between the data transmitting apparatus and the data receiving apparatus is short enough that the data receiving apparatus can obtain sufficient reception electric field intensity, the user is allowed to perform an operation to lower the transmission power of the data transmitting apparatus. In this manner, other receiving apparatuses located around this data receiving apparatus have difficulties receiving the packets transmitted from the data transmitting apparatus, as a result of which data leakage or wiretapping can be suppressed and security improved.

According to the second embodiment of the present invention, the threshold value is determined depending on a reception condition of the packet. Such a data receiving apparatus, which varies the threshold value, for example, for the reception condition where the possibility of leakage or wiretapping is relatively high and for the reception condition where the possibility of leakage or wiretapping is relatively low, makes it more likely for the assistance information relating to the operation of regulating the transmission power to be output in the former condition than in the latter. This effectively reduces the risk of data leakage or wiretapping. On the other hand, under the latter condition, the assistance information relating to the operation of regulating the transmission power is less likely to be output. Thus, the data deficit is suppressed in the data receiving apparatus while security remains assured, and a high quality of data reception can be maintained.

According to the third embodiment of the present invention, the reception condition is a condition based on at least one of a position of the data receiving apparatus at a time of receiving the packet and a reception time/date of the packet. Such a data receiving apparatus can set a threshold value in accordance with the possibility of wiretapping estimated from at least one of the position and reception time/date.

According to the fourth embodiment of the present invention, the threshold value is determined depending on properties of data stored in the packet. Such a data receiving apparatus, which varies the threshold value, for example, for data which would create a relatively large amount of damage at the time of third-party interception and for data which would create a relatively small amount of damage at the time of third-party interception, makes it more likely for the assistance information relating to the operation of regulating the transmission power to be output for the former data than the latter. This effectively reduces the risk of data leakage or wiretapping. On the other hand, for the latter data, the assistance information relating to the operation of regulating the transmission power is less prone to be output. Thus, the data deficit is suppressed in the data receiving apparatus while security remains assured, and a high quality of data reception can be maintained.

According to the fifth embodiment of the present invention, the packet includes a first packet in which biological data is stored. Such a data receiving apparatus can be used for transmission of biological data such as blood pressure data.

According to the sixth embodiment of the present invention, a data transmitting apparatus includes: a transmitter configured to transmit a one-way communication packet; an input unit configured to receive user input for instructing an increase or decrease of transmission power; and a transmission controller configured to control the transmission power of the transmitter in accordance with the user input. With such a data transmitting apparatus, even if only the one-way communication transmission function is provided, the transmission power can be controlled in accordance with the user input. In other words, the security can be enhanced by suppressing the data leakage or wiretapping.

The present invention can offer a technique for suppressing the leakage of the data transmitted via one-way communication.

BRIEF DESCRIPTION OF THE DRAWINGS

FIG. 8 is an explanatory diagram of exemplary threshold values determined for use by the data receiving apparatus according to the present embodiment.

FIG. 9 is an explanatory diagram of exemplary threshold values determined for use by the data receiving apparatus according to the present embodiment.

FIG. 10 is an explanatory diagram of advertising performed in BLE.

FIG. 11 is a diagram showing an exemplary data structure of a packet transmitted and received in BLE.

FIG. 12 is a diagram showing an exemplary data structure of the PDU field of an advertisement packet.

DETAILED DESCRIPTION

Figure 1:
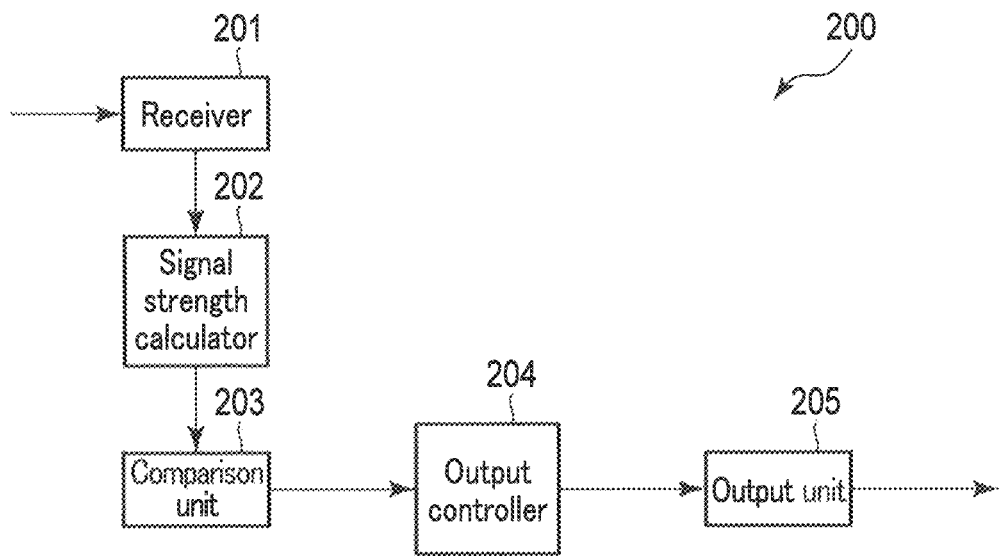
FIG. 1 is a block diagram showing an application example of a data receiving apparatus according to the present embodiment.

An embodiment according to an aspect of the present invention (hereinafter also referred to as "the present embodiment") will be described below with reference to the drawings.

The elements that are the same as or similar to the ones that have already been explained are indicated by the same or similar reference numerals, and the overlapping descriptions are basically omitted.

The purpose of the present embodiment is to provide a technique for suppressing the leakage of the data transmitted in one-way communication.

§ 1 Application Examples

First, an application example of the present invention will be described with reference to FIG. 1. An application example of the data receiving apparatus 200 according to the present embodiment is schematically shown in FIG. 1. The data receiving apparatus 200 includes at least a receiver 201, a signal strength calculator 202, a comparison unit 203, an output controller 204, and an output unit 205.

The receiver 201 receives a radio signal carrying a packet for one-way communication, which will be described later, from a data transmitting apparatus 100 (packet transmitting device) that is not shown in FIG. 1. The receiver 201 performs reception processing including low-noise amplification, filtering, down-conversion, and the like, on the radio signal to obtain a reception signal of an intermediate frequency band or baseband. The receiver 201 sends this reception signal to the signal strength calculator 202.

The signal strength calculator 202 calculates the signal strength (e.g., reception signal strength indication (RSSI)) of the reception signal from the receiver 201. The signal strength calculator 202 sends this signal strength to the comparison unit 203.

The comparison unit 203 receives the signal strength from the signal strength calculator 202 and compares it with a threshold value. The threshold value is defined as a reference value for determining whether or not there is a possibility of wiretapping the packet. The comparison unit 203 sends the comparison result to the output controller 204.

The threshold value may be fixed. Alternatively, the threshold value may be variably determined in accordance with the packet reception conditions (e.g., inside the house or public place) or the data properties stored in the packet (e.g., whether or not it is encrypted), as described below.

The output controller 204 receives the comparison result from the comparison unit 203. If the signal strength exceeds the threshold value, the transmission power may be excessive, or in other words, there may be a possibility of packet wiretapping (or interception) by a third party. Here, wiretapping denotes interception of a packet and, if the packet is encrypted, decryption of the packet.

However, if the data transmitting apparatus 100 is provided with the above-described one-way communication transmission function only, the transmission power of the data transmitting apparatus 100 cannot be remotely controlled by the data receiving apparatus 200 or any other apparatus. For this reason, the output controller 204 generates assistance information relating to the operation for reducing the transmission power of the packet transmitting device, or in other words, assistance information that prompts the user input which is then output by the output unit 205. With a focus on this function, the output unit 205 may also be referred to as a "generation unit" or an "assistance information generation unit".

The assistance information contains data (alert data, e.g., a text, image or voice) to alert the user to the possibility of the transmission power of the data transmitting apparatus 100 being excessively large and the possibility that a third party may wiretap (or intercept) the data transmitted from the data transmitting apparatus 100.

In addition, the assistance information may include data representing the operation procedure required for the user to reduce the transmission power of the data transmitting apparatus 100. By outputting such assistance information, the user may avoid the need to consult the instruction manual of the data transmitting apparatus 100.

Thus, the data receiving apparatus 200 outputs assistance information when the signal strength of the reception signal exceeds the threshold value. As a result, the user can obtain significant information regarding wireless data transmission that is difficult to notice (e.g., the possibility of the transmission power of the data transmitting apparatus 100 being too large and the possibility of the data from the data transmitting apparatus 100 being wiretapped (or intercepted) by a third party). Furthermore, even if the data transmitting apparatus 100 is provided only with the one-way communication transmission function, the transmission power of the data transmitting apparatus 100 can be suitably controlled through use of the user input triggered by the assistance information.

§ 2 Exemplary Structure

[Hardware Structure]
<Data Receiving Apparatus>

Figure 4:
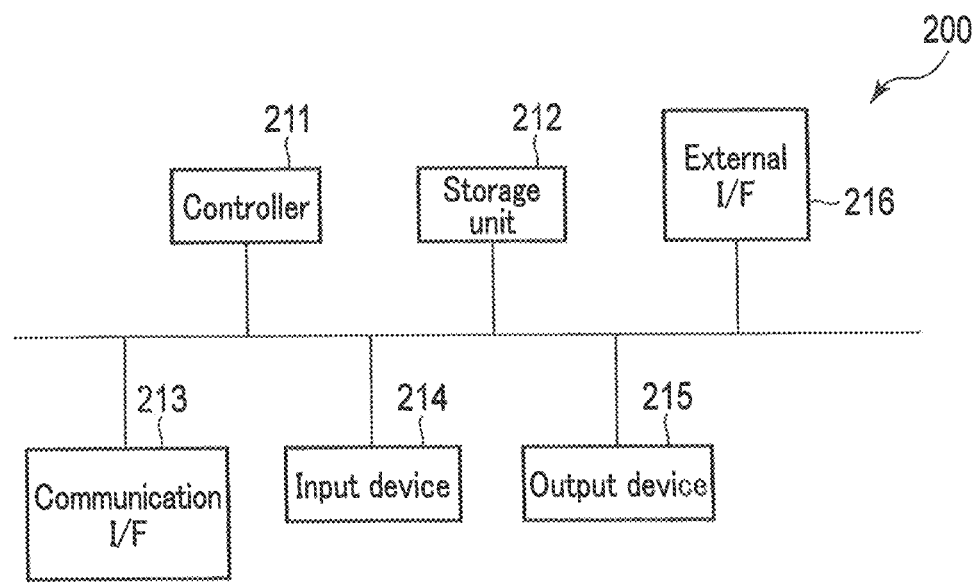
FIG. 4 is a block diagram showing an exemplary hardware structure of the data receiving apparatus according to the present embodiment.

Next, by referring to FIG. 4, an exemplary hardware structure of the data receiving apparatus 200 according to the present embodiment will be described. FIG. 4 schematically shows an exemplary hardware structure of the data receiving apparatus 200.

As shown in FIG. 4, the data receiving apparatus 200 is a computer, typically a smartphone, in which a controller 211, a storage unit 212, a communication interface 213, an input device 214, an output device 215, and an external interface 216 are electrically connected to each other. In FIG. 4, the communication interface and external interface are denoted as "communication I/F" and "external I/F", respectively.

The controller 211 includes a central processing unit (CPU), a random access memory (RAM), a read only memory (ROM), and the like. The CPU expands a program stored in the storage unit 212 into the RAM. When the CPU interprets and executes this program, the controller 211 can implement various types of information processing (processing of function blocks described under the section "Software Structure").

The storage unit 212 is an auxiliary storage device, which may be a semiconductor memory such as a built-in or externally provided flash memory. The storage unit 212 stores programs to be executed by the controller 211, data to be used by the controller 211 (e.g., identifiers, time/date data, sensor data, and assistance information) and the like. If the data receiving apparatus 200 is a laptop or desktop computer, the storage unit 212 may be a hard disk drive (HDD), a solid state drive (SSD), or the like.

The communication interface 213 includes various wireless communication modules mainly for BLE, mobile communication (3G, 4G, etc.) and WLAN, and is to perform wireless communication via a network. The communication interface 213 may further include a wired communication module such as a wired LAN module.

The input device 214 may be a touch screen, a keyboard, a mouse and the like, through which the user input is received. The output device 215 may be a display or a speaker, through which outputting is realized.

The external interface 216 may be a universal serial bus (USB) port, a memory card slot and the like, and is an interface for establishing a connection to an external device.

In an actual hardware structure of the data receiving apparatus 200, structural components may be omitted, replaced, and added as appropriate, according to the embodiment. For example, the controller 211 may include a plurality of processors. The data receiving apparatus 200 may be composed of a plurality of information processing apparatuses. The data receiving apparatus 200 may be an information processing apparatus specially designed for a service to be provided, or otherwise a general-purpose desktop personal computer (PC), tablet PC or the like.

<Data Transmitting Apparatus>

Figure 7:
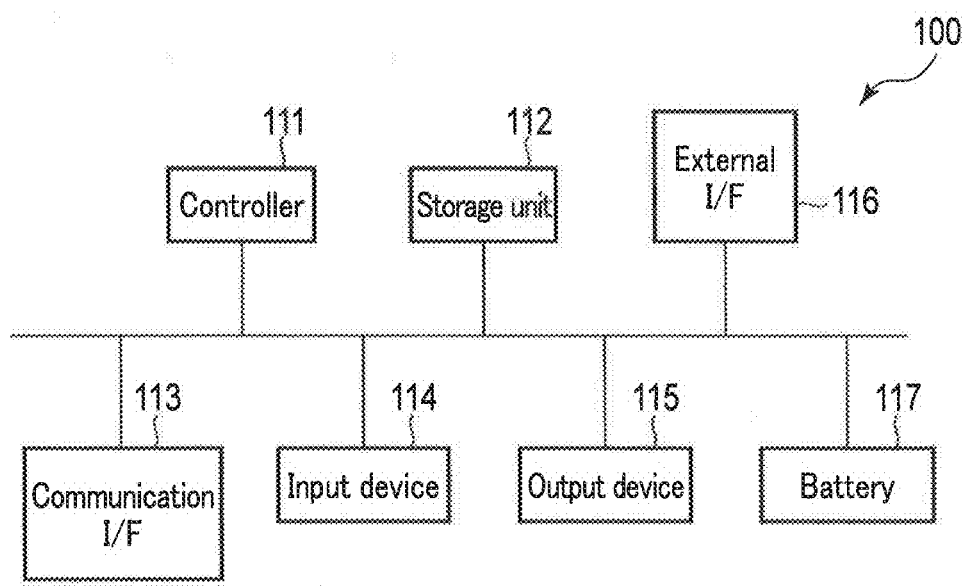
FIG. 7 is a block diagram showing an exemplary hardware structure of the data transmitting apparatus according to the present embodiment.

Next, by referring to FIG. 7, an exemplary hardware structure of the data transmitting apparatus 100 according to the present embodiment will be described. FIG. 7 schematically shows an exemplary hardware structure of the data transmitting apparatus 100.

As shown in FIG. 7, the data transmitting apparatus 100 is a computer in which a controller 111, a storage unit 112, a communication interface 113, an input device 114, an output device 115, an external interface 116, and a battery 117 are electrically connected to each other. Typically, it is a sensor device that regularly measures a quantity related to a user's biological information or activity information, such as a blood pressure monitor, a thermometer, an activity tracker, a pedometer, a body composition scale, a weight scale, and the like. In FIG. 7, the communication interface and external interface are denoted as "communication I/F" and "external I/F", respectively.

The controller 111 includes a CPU, RAM, ROM, and the like. The CPU expands a program stored in the storage unit 112 into the RAM. When the CPU interprets and executes this program, the controller 111 can implement various types of information processing, such as processing of the function blocks described under the section "Software Structure".

The storage unit 112 is an auxiliary storage device, which may be a semiconductor memory such as a built-in or externally provided flash memory, HDD, or SSD. The storage unit 112 stores programs to be executed by the controller 111, data to be used by the controller 111 (e.g., sensor data) and the like.

The communication interface 113 includes at least a wireless module such as BLE that can realize one-way communication. The input device 114 may include a device through which the user input is received, such as a touch screen, buttons and switches, and a sensor for detecting a quantity related to the user's biological information or activity information. The output device 115 may be a display or a speaker, through which outputting is realized.

The external interface 116 may be a USB port, a memory card slot, and is an interface for establishing a connection to an external device.

The battery 117 supplies the power supply voltage of the data transmitting apparatus 100. The battery 117 may be replaceable. The data transmitting apparatus 100 may be connectable to a commercial power supply by way of an alternating current (AC) adapter. If this is the case, the battery 117 may be omitted.

In an actual hardware structure of the data transmitting apparatus 100, structural components may be omitted, replaced, and added as appropriate, according to the embodiment. For example, the controller 111 may include a plurality of processors. The data transmitting apparatus 100 may be composed of a plurality of sensor devices.

[Software Structure]

<Data Receiving Apparatus>

Figure 2:
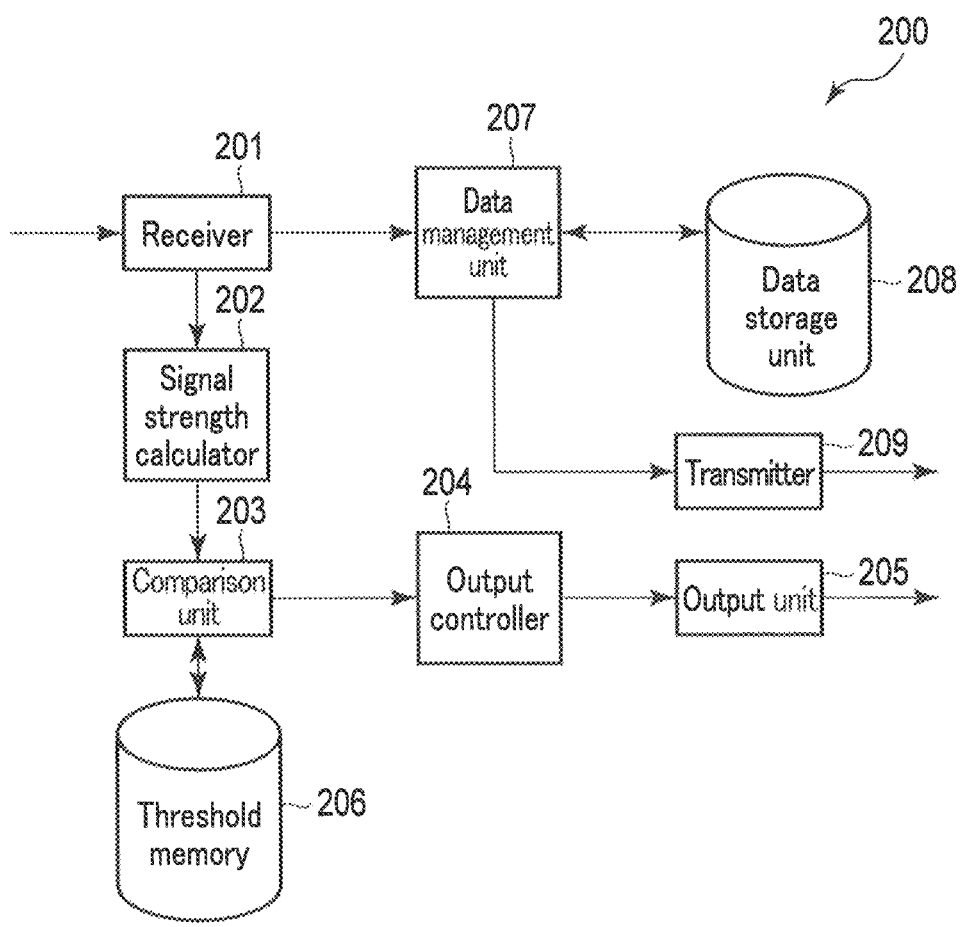
FIG. 2 is a block diagram showing an exemplary software structure of the data receiving apparatus according to the present embodiment.

Next, by referring to FIG. 2, an exemplary software structure of the data receiving apparatus 200 according to the present embodiment will be described. FIG. 2 schematically shows an exemplary software structure of the data receiving apparatus 200.

The controller 211 in FIG. 4 expands a program stored in the storage unit 212 into the RAM. The controller 211 interprets and executes this program by the CPU and thereby controls various hardware components shown in FIG. 4. In this manner, the data receiving apparatus 200 functions as a computer that includes a receiver 201, a signal strength calculator 202, a comparison unit 203, an output controller 204, an output unit 205, a threshold memory 206, a data management unit 207, a data storage unit 208, and a transmitter 209, as illustrated in FIG. 2.

The receiver 201 receives a radio signal that carries a packet including, for example, sensor data and time/date data associated with this sensor data, from the data transmitting apparatus 100. This packet may be a BLE advertisement packet. It is possible, however, that BLE may be replaced with some other low-power consuming and one-way communication standards in the future. In such a case, the replacement may be introduced to the following description as appropriate.

Here, the BLE advertisement will be briefly described.

In the passive scanning scheme adopted in BLE, a new node regularly transmits an advertisement packet to inform its presence, as illustrated in FIG. 10. This new node can save power consumption by entering a low-power consuming sleep mode between the transmission of one advertisement packet and the next transmission. With the advertisement packet receiving side also performing intermittent operations, a nominal amount of power is consumed in association with the transmission and reception of an advertisement packet.

FIG. 11 shows the basic structure of a BLE wireless communication packet. A BLE wireless communication packet contains a 1-byte preamble, a 4-byte access address, a 2- to 39-byte (variable) protocol data unit (PDU), and a 3-byte cyclic redundancy checksum (CRC). The length of BLE wireless communication packet is 10 to 47 bytes, depending on the length of PDU. A 10-byte BLE wireless communication packet (with a 2-byte PDU), also referred to as an "empty PDU packet", is regularly exchanged between the master and slave.

A preamble field is prepared for synchronization of BLE wireless communication, in which "01" or "10" is repeatedly stored. As an access address, a fixed value is stored for an advertising channel, while a random number is stored for the data channel. In the present embodiment, an advertisement packet that is a BLE wireless communication packet transmitted on the advertising channel is dealt with. A CRC field is used for detection of reception errors. The CRC calculation is limited to the PDU field.

Next, the PDU field of an advertisement packet will be described with reference to FIG. 12. The PDU field of a data communication packet, which is a BLE wireless communication packet transmitted on the data channel, has a data structure different to that of FIG. 12. However, the present embodiment is not directed to a data communication packet, and the description thereof is omitted.

The PDU field of an advertisement packet includes a 2-byte header and a 0- to 37-byte (variable) payload. Furthermore, the header includes a 4-bit PDU Type field, a 2-bit unused field, a 1-bit TxAdd field, a 1-bit RxAdd field, a 6-bit Length field, and a 2-bit unused field.

The PDU Type field stores a value indicative of this PDU Type. Values have been defined, for example, for "connectable advertising" and "disconnected advertising". In the TxAdd field, a flag indicative of whether or not the payload includes a transmission address is stored. In a similar manner, in the RxAdd field, a flag indicative of whether or not the payload includes a reception address is stored. In the Length field, a value indicative of the payload byte size is stored.

In the payload, any kind of data can be stored. The data transmitting apparatus 100 therefore stores sensor data and time/date data in the payload, using a predetermined data structure. This data structure includes, for example, an identifier that identifies a user, an identifier that identifies a data transmitting apparatus 100 that is a sender device, an identifier that identifies a data receiving apparatus 200 that is a destination device, time/date data, and one or more types of sensor data such as systolic blood pressure, diastolic blood pressure, pulse rate, and activity amount associated with the time/date data.

Returning to the description of the software structure of the data receiving apparatus 200, the receiver 201 executes reception processing including low-noise amplification, filtering, and down-conversion, on the radio signal to obtain a reception signal of an intermediate frequency band or baseband. The receiver 201 sends this reception signal to the signal strength calculator 202.

The receiver 201 further executes demodulating and decoding on the reception signal to reproduce the BLE advertisement packet transmitted from the data transmitting apparatus 100. Then, the receiver 201 extracts the PDU payload from the BLE advertisement packet.

The receiver 201 may check an identifier (indicative of a sensor data sender device or a valid destination) included in the payload, and, if the value of the identifier is invalid, the receiver 201 may discard the received packet. On the other hand, if the value of the identifier is valid, the receiver 201 sends the extracted sensor data and time/date data to the data management unit 207.

The signal strength calculator 202 calculates the signal strength (for example, RSSI) of the reception signal from the receiver 201. The signal strength calculator 202 sends this signal strength to the comparison unit 203.

The comparison unit 203 receives the signal strength from the signal strength calculator 202 and reads the threshold value from the threshold memory 206. The comparison unit 203 compares the signal strength with the threshold value, and sends the comparison result to the output controller 204.

As mentioned above, the threshold value may be variable. Some examples of the determination of a threshold value are discussed below.

In the first example, a threshold value may be determined depending on the packet reception condition. Packet reception conditions may be divided, for example, into a reception condition with a possibility of wiretapping being relatively high (Public) and a reception condition with such a possibility being low (Private). The reception condition may be determined as Private, for example, when the positional data of the data receiving apparatus 200 at the time of receiving a packet indicates a predetermined location (e.g., the user's home), when the packet reception time/date is within a predetermined range (for example, during the user's sleep hours), or when the user explicitly inputs "Private" into the setting of the reception condition. On the other hand, the Public reception condition may simply cover all the reception conditions not falling under Private. Alternatively, in a manner similar to Private, the Public reception condition may be determined based on the location of the data receiving apparatus 200 at the time of receiving the packet, the reception time and date of the packet, user input, and the like.

The comparison unit 203 uses a smaller threshold in the reception condition with a relatively high possibility of wiretapping (Public) than in the reception condition with a low possibility (Private). For example, the comparison unit 203 may extract the threshold value Th1 or Th2 from the table (stored in the threshold memory 206) illustrated in FIG. 8, using the reception condition. In this example, Th1<Th2.

In the above manner, by changing the threshold value between the reception condition with a relatively high possibility of wiretapping (Public) and the reception condition with a low possibility (Private), the transmission power can be regulated under the Public condition to prevent wiretapping, while the regulation of the transmission power can be eased under the Private condition to prevent data deficit, which tends to occur when a reception fails at the data receiving apparatus 200. The reception conditions may be classified into three levels or more, and the threshold value may also be set to three levels or more.

In the second example, the threshold value may be determined depending on the properties of the data stored in a packet. The data stored in a packet may be divided into, for example, data that would involve a relatively large amount of damage and data that would involve a small amount of damage were a third party to intercept it. Here, an amount of damage in case of third-party interception may be evaluated as a risk that involves information needing to be concealed, such as that pertaining to the user's health condition, possibly being leaked to the third party. Data with a relatively large amount of damage in case of third-party interception may be unencrypted sensor data. On the other hand, data with a relatively small amount of damage in case of third-party interception may be encrypted sensor data, or unencrypted data that need not be concealed.

The comparison unit 203 uses a smaller threshold value for the data with a relatively large amount of damage in case of third-party interception than the data with a relatively small amount of damage in case of third-party interception. The comparison unit 203 may extract the threshold Th3 or Th4 from the table (stored in the threshold memory 206) illustrated in FIG. 9, using the data property. In this example, Th3<Th4.

In the above manner, by changing the threshold value for data with a relatively large amount of damage in case of third-party interception and for data with a relatively small amount of damage in case of third-party interception, the transmission power can be regulated to prevent wiretapping in the former case, while in the latter case, the regulation of the transmission power can be eased to prevent data deficit which tends to occur when the reception fails at the data receiving apparatus 200. The data type may be classified into three levels or more, and the threshold value may be set to three levels or more.

In addition to the above, the first and second examples may be combined. For example, the comparison unit 203 may obtain the arithmetic average of the threshold value determined based on the packet reception condition and the threshold value determined based on the data property, and determine this as the final threshold value.

The output controller 204 receives the comparison result from the comparison unit 203. If the signal strength exceeds the threshold value, the output controller 204 generates assistance information relating to the operation for lowering the transmission power of the packet transmitting device, or in other words, assistance information for prompting the user input. The output controller 204 sends the assistance information to the output unit 205. As described above, the assistance information includes data (alert data) for alerting the user, and may further include any data to be transmitted to the user regarding the operation procedure required to lower the transmission power.

The output unit 205 receives the assistance information from the output controller 204 and outputs this information. The user who has noticed the output assistance information is prompted to operate the data transmitting apparatus 100 to lower the transmission power.

The threshold memory 206 stores one or more threshold values. The threshold value stored in the threshold memory 206 is read by the comparison unit 203, as needed.

The data management unit 207 receives the time/date data and the sensor data from the receiver 201, and writes the data in association with each other into the data storage unit 208. The data management unit 207 further reads the set of time/date data and sensor data stored in the data storage unit 208 in accordance with a command, for example, from a host application (not shown) (e.g., biological data management application), and transmits the set to the transmitter 209 or a display (not shown).

The data storage unit 208 has its set of time/date data and sensor data read and written therein by the data management unit 207.

Figure 3:
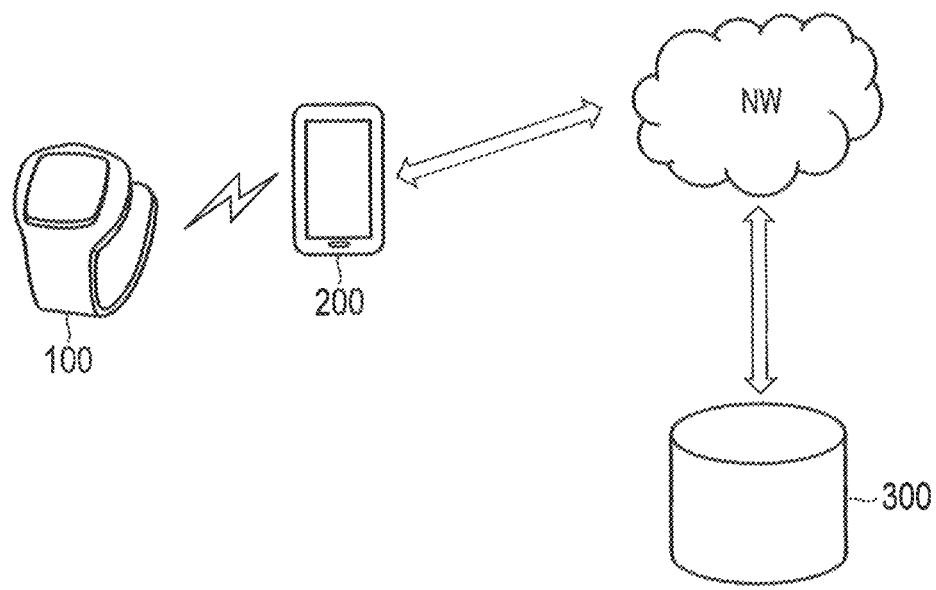
FIG. 3 is a diagram showing an exemplary data transmission system including a data transmitting apparatus and data receiving apparatus according to the present embodiment.

The transmitter 209 receives the set of time/date data and sensor data from the data management unit 207, and transmits it to the server 300 via a network (see FIG. 3). The transmitter 209 employs mobile communication or WLAN, for example. In the example of FIG. 3, the appearance of a wearable blood pressure monitor of a wristwatch type is illustrated as the data transmitting apparatus 100. However, the appearance of the data transmitting apparatus 100 is not limited to this type and may be a blood pressure monitor of a stationary type, or a sensor device that measures quantities relating to any other type of biological or activity information.

The server 300 corresponds to a database that manages the sensor data (mainly biological data) of a large number of users. The server 300 may be configured to transmit the biological data of a user in response to an act of access from the user himself/herself, and in addition, to an act of access from the PCs of, for example, wellness instructors, insurance companies, or program organizers for the purpose of delivering wellness guidance to the user, insurance enrollment assessment, performance evaluation of a wellness promotion program and the like.

<Data Transmitting Apparatus>

Figure 6:
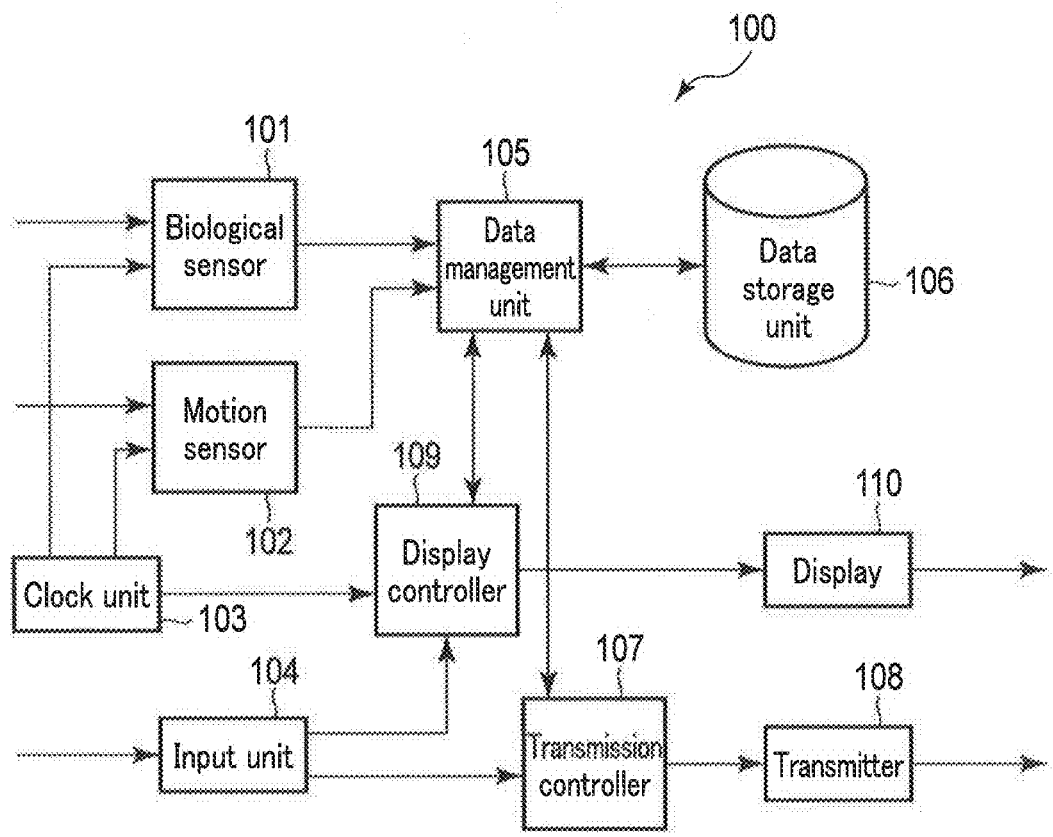
FIG. 6 is a block diagram showing an exemplary software structure of the data transmitting apparatus according to the present embodiment.

Next, by referring to FIG. 6, an example of the software structure of the data transmitting apparatus 100 according to the present embodiment will be described. FIG. 6 schematically shows an example of the software structure of the data transmitting apparatus 100.

The controller 111 of FIG. 7 expands the program stored in the storage unit 112 into the RAM. The controller 111 interprets and executes this program by the CPU to control various hardware components shown in FIG. 7. As a result, the data transmitting apparatus 100 functions as a computer including the biological sensor 101, motion sensor 102, clock unit 103, input unit 104, data management unit 105, data storage unit 106, transmission controller 107, transmitter 108, display controller 109, and display 110, as shown in FIG. 6.

The biological sensor 101 obtains biological data by measuring quantities relating to the user's biological information. The operation of the biological sensor 101 is controlled, for example, by a sensor controller (not shown). The biological sensor 101 sends the biological data to the data management unit 105, in association with the time/date data received from the clock unit 103. Typically, the biological sensor 101 includes a blood pressure sensor that obtains blood pressure data by measuring a user's blood pressure. If this is the case, the biological data includes blood pressure data. The blood pressure data may include, but is not limited to, systolic and diastolic blood pressure values and pulse rate. In addition, the biological data may include electrocardiographic data, pulse wave data, body temperature data, and the like.

The blood pressure sensor may include a blood pressure sensor (hereinafter referred to as a "continuous blood pressure sensor") configured to continuously measure a user's blood pressure for every beat. The continuous blood pressure sensor may continuously measure the user's blood pressure from Pulse Transit Time (PTT), or may realize continuous measurement by tonometry or any other technique.

In place of, or in addition to, the continuous blood pressure sensor, the blood pressure sensor may include a blood pressure sensor not designed for continuous measurement (hereinafter referred to as an "intermittent blood pressure sensor"). An intermittent blood pressure sensor may use a cuff as a pressure sensor to measure the user's blood pressure (oscillometric method).

Intermittent blood pressure sensors (in particular, oscillometric blood pressure sensors) tend to demonstrate higher measurement accuracy than continuous blood pressure sensors. Therefore, in response to a certain condition that is satisfied (e.g., a condition that the user's blood pressure data measured by a continuous blood pressure sensor suggests a certain state), the blood pressure sensor may activate an intermittent blood pressure sensor in place of the continuous blood pressure sensor, thereby measuring the blood pressure data with a higher degree of accuracy.

The motion sensor 102 may be an acceleration sensor or a gyro sensor. The motion sensor 102 detects the acceleration/angular velocity exerted on the motion sensor 102, and thereby obtains triaxial acceleration/angular velocity data. The operation of the motion sensor 102 may be controlled by a sensor controller (not shown). This acceleration/angular velocity data can be used for estimation of the activity state (posture and/or motion) of the user wearing the data transmitting apparatus 100. The motion sensor 102 associates the acceleration/angular velocity data with the time/date data received from the clock unit 103, and sends it to the data management unit 105.

Either one of the biological sensor 101 or the motion sensor 102 may be omitted. In addition to, or in place of, the biological sensor 101 and the motion sensor 102, an environmental sensor may be arranged. The environmental sensor may include a temperature sensor, a humidity sensor, an atmospheric pressure sensor, and the like. That is, for the sensor data, the sensor measures a predetermined physical quantity, and any data generated based on the measurement result may be sensor data.

The clock unit 103 indicates the time and date. The clock unit 103 includes, for example, a crystal oscillator that vibrates at a fixed frequency, a frequency dividing circuit that divides the output of the crystal oscillator to obtain a 1-Hz signal, and a counter that counts this signal to obtain a serial value indicating the time and date. The clock unit 103 sends the time/date data (e.g., the above-mentioned serial value) indicating the current time and date to the biological sensor 101 and the motion sensor 102. The time/date data may be used as the measurement time and date of the biological data measured by the biological sensor 101, and the measurement time and date of the acceleration/angular velocity data measured by the motion sensor 102. In addition, the time/date data is referred to by the display controller 109 for displaying on the display 110.

The clock unit 103 (or the serial values held by the clock unit 103) may be designed to be adjustable (for accurate time) in accordance with the user input. Alternatively, such a design may be left out so as to simplify the input device 114 (with fewer buttons and the like required). Even with such a design, it is possible to demonstrate to the user a relative time and date based on the current time and date, in such a manner as "10 minutes ago", "2 hours ago", "yesterday", and "1 week ago".

The input unit 104 receives user input. The user input may be for the purposes of control of the data transmission by the transmitter 108, for control of the data display by the display 110, or for initiation of the measurement by the biological sensor 101 or the motion sensor 102.

The user input for controlling the data transmission by the transmitter 108 may explicitly or implicitly instruct the transmission of a set of specific time/date data and sensor data, or an increase or decrease in the transmission power.

The input unit 104 sends the user input for controlling the data transmission by the transmitter 108, to the transmission controller 107; the user input for controlling the data display by the display 110, to the display controller 109; and the user input for initiating the measurement by the biological sensor 101 or motion sensor 102, to a sensor controller (not shown).

The data management unit 105 receives the sensor data (biological data or acceleration/angular velocity data) associated with the time/date data from the biological sensor 101 or the motion sensor 102, and writes the data to the data storage unit 106. The data management unit 105 may automatically send the data to the transmission controller 107 or the display controller 109, when the time/date data and sensor data are newly received. Furthermore, in response to an instruction from the transmission controller 107 or the display controller 109, the data management unit 105 may read the set of time/date data and sensor data stored in the data storage unit 106, and send it to the transmission controller 107 or the display controller 109.

The data storage unit 106 has its set of time/date data and sensor data read and written therein by the data management unit 105.

The transmission controller 107 receives the set of time/date data and sensor data from the data management unit 105, and generates a BLE advertisement packet as described with reference to FIGS. 11 and 12. The transmission controller 107 sends the generated advertisement packet to the transmitter 108. Furthermore, the transmission controller 107 controls the transmission power of the transmitter 108.

The transmission controller 107 may receive the user input for controlling the data transmission by the transmitter 108, from the input unit 104. If this is the case, the transmission controller 107 may increase or decrease the transmission power for the transmitter 108, or request a set of specific time/date data and sensor data from the data management unit 105 based on the user input. In addition, regardless of the user input, the transmission controller 107 may generate an advertisement packet for resending the previously transmitted data or for notifying the latest time/date data available.

The transmitter 108 receives the BLE advertisement packet from the transmission controller 107, and transmits (advertises) this advertisement packet in accordance with the transmission power determined by the transmission controller 107.

The display controller 109 receives the set of time/date data and sensor data from the data management unit 105, based on which the display controller 109 generates display data for the display 110. The display controller 109 may refer to the clock unit 103 and generate the display data for displaying the time/date data held by the clock unit 103 on the display 110. The display controller 109 may further generate the display data for the purposes of displaying on the display 110 the transmission power determined for the transmitter 108. The display controller 109 sends the generated display data to the display 110.

The display controller 109 may receive the user input for the purposes of controlling the data display by the display 110, from the input unit 104. If this is the case, the display controller 109 may request, in accordance with the user input, the set of specific time/date data and sensor data from the data management unit 105, or the latest time/date data available from the clock unit 103.

The display 110 receives the display data from the display controller 109 and displays this data.

<Others>

The functions of the data receiving apparatus 200 will be described in detail under the section "Examples of Operation" below. In the present embodiment, an example of each of the functions of the data transmitting apparatus 100 and the data receiving apparatus 200 being realized by a general-purpose CPU is described. However, part or all of the above functions may be realized by one or more dedicated processors. Moreover, regarding the software structures of the data transmitting apparatus 100 and the data receiving apparatus 200, the functions may be omitted, replaced, or added as appropriate according to the embodiment.

§ 3 Examples of Operation

<Data Receiving Apparatus>

Figure 5:
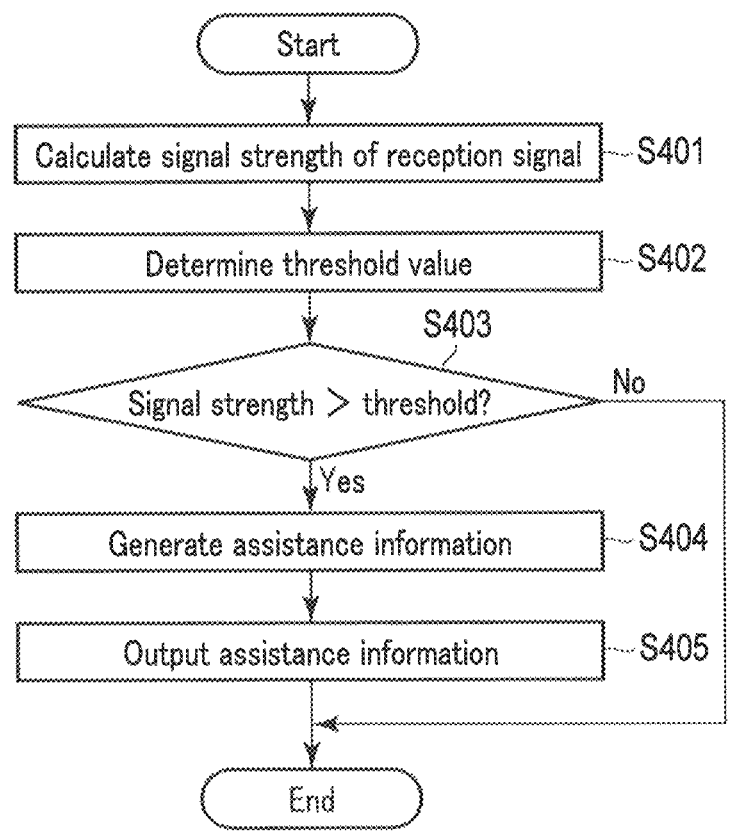
FIG. 5 is a flowchart showing an exemplary operation of the data receiving apparatus according to the present embodiment.

Next, by referring to FIG. 5, an exemplary operation of the data receiving apparatus 200 will be described. FIG. 5 is a flowchart illustrating an exemplary operation of the data receiving apparatus 200. The processing procedure is described below merely as an example, and each operation may be modified as needed. Furthermore, in the processing procedure described below, steps may be omitted, replaced, and added as needed according to the embodiment.

In the operation example of FIG. 5, the operation is initiated when the receiver 201 of the data receiving apparatus 200 receives a radio signal carrying a BLE advertisement packet from the data transmitting apparatus 100 and obtains a reception signal.

The signal strength calculator 202 calculates the signal strength of the reception signal (step S401). The comparison unit 203 determines a threshold value to compare with the signal strength calculated at step S401 (step S402). Specifically, as described above, the comparison unit 203 may determine the threshold value according to the reception condition of the packet, the property of the data stored in the packet, and the like. If the threshold value is fixed, the comparison unit 203 simply reads the threshold value from the threshold memory 206.

The comparison unit 203 compares the signal strength calculated at step S401 with the threshold value determined at step S402 (step S403). If the signal strength exceeds the threshold value, the process proceeds to step S404; otherwise, the process is terminated.

At step S404, the output controller 204 generates assistance information. Thereafter, the output unit 205 outputs the assistance information generated at step S404, and the process is terminated.

[Operations and Effects]

As described above, the data receiving apparatus according to the present embodiment receives a radio signal carrying a one-way communication packet transmitted from the data transmitting apparatus, and compares the signal strength with a threshold value, thereby evaluating as to whether or not the transmission power of the data transmitting apparatus is excessive. If the data receiving apparatus evaluates that the transmission power of the data transmitting apparatus is too large, the data receiving apparatus outputs assistance information relating to an operation for lowering the transmission power of the data transmitting apparatus, that is, assistance information for prompting the user to make such input. Therefore, according to this data receiving apparatus, even if the data transmitting apparatus is provided only with a one-way communication transmission function, the transmission power of the data transmitting apparatus can be suitably lowered through use of the user input made in response to assistance information. In other words, security can be enhanced by suppressing the data leakage or wiretapping.

All the above embodiments are described merely as examples of the present invention in every aspect. Naturally, various improvements and modifications can be made without departing from the scope of the present invention. In other words, in the implementation of the present invention, a specific configuration according to the embodiment may be adopted as appropriate. The data dealt with in each embodiment has been described in natural language; however, to be specific, the data is designated by a computer-recognizable pseudo language, commands, parameters, a machine language, or the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

§ 4 Modification Examples

As mentioned above, the embodiments of the present invention have been described in detail. The above descriptions are only examples of this invention in every aspect. Naturally, various improvements and modifications can be made without departing from the scope of the present invention.

§ 5 Supplementary Notes

Part or all of each embodiment above can be described as shown in, but not in ways limited to, the following supplementary notes in addition to the claims.

(Supplementary Note 1)

A data receiving apparatus comprising:
a memory; and
a processor coupled to the memory,
wherein the processor is configured to function as:
(a) a receiver that receives a one-way communication packet transmitted from a data transmitting apparatus;
(b) a calculator that calculates a reception signal strength of the packet at the receiver;
(c) a comparison unit that compares the calculated reception signal strength with a threshold value;
(d) a generation unit that generates assistance information relating to an operation for the lowering of transmission power of the data transmitting apparatus if a result of the comparison demonstrates that the reception signal strength exceeds a threshold value; and
(e) an output unit that outputs the generated assistance information.

(Supplementary Note 2)

A data transmitting apparatus comprising:
a memory; and
a processor coupled to the memory,
wherein the processor is configured to function as:
(a) a transmitter that transmits a one-way communication packet;
(b) an input unit that receives user input for instructing an increase or decrease of transmission power; and
(c) a transmission controller that controls the transmission power of the transmitter in accordance with the user input.

REFERENCE SIGNS LIST

100 Data transmitting apparatus
101 Biological sensor
102 Motion sensor
103 Clock unit
104 Input unit
105, 207 Data management unit
106, 208 Data storage unit
107 Transmission controller
108, 209 Transmitter
109 Display controller
110 Display
111, 211 Controller
112, 212 Storage unit
113, 213 Communication interface
114, 214 Input device
115, 215 Output device
116, 216 External interface
117 Battery
200 Data receiving apparatus
201 Receiver
202 Signal strength calculator
203 Comparison unit
204 Output controller
205 Output unit
206 Threshold memory
300 Server

The invention claimed is:

1. A data receiving apparatus comprising:
a receiver configured to receive a one-way communication packet transmitted from a data transmitting apparatus, the packet including sensor data measured by the data transmitting apparatus;
a calculator configured to calculate a reception signal strength of the packet at the receiver;
a comparison unit configured to compare the calculated reception signal strength with a threshold value;
a generation unit configured to generate assistance information relating to an operation for lowering transmission power of the data transmitting apparatus if the reception signal strength exceeds a threshold value, as a result of the comparison; and
an output unit configured to output the generated assistance information, wherein
the threshold value is determined depending on a reception condition of the packet, and
the reception condition is a condition based on at least one of a position of the data receiving apparatus at a time of receiving the packet and a reception time/date of the packet.

2. A data receiving apparatus comprising:
a receiver configured to receive a one-way communication packet transmitted from a data transmitting apparatus, the packet including sensor data measured by the data transmitting apparatus;
a calculator configured to calculate a reception signal strength of the packet at the receiver;
a comparison unit configured to compare the calculated reception signal strength with a threshold value;
a generation unit configured to generate assistance information relating to an operation for lowering transmission power of the data transmitting apparatus if the reception signal strength exceeds a threshold value, as a result of the comparison; and
an output unit configured to output the generated assistance information, wherein
the threshold value is determined depending on properties of data stored in the packet.

3. A data receiving apparatus comprising:
a receiver configured to receive a one-way communication packet transmitted from a data transmitting apparatus, the packet including sensor data measured by the data transmitting apparatus;
a calculator configured to calculate a reception signal strength of the packet at the receiver;
a comparison unit configured to compare the calculated reception signal strength with a threshold value;
a generation unit configured to generate assistance information relating to an operation for lowering transmission power of the data transmitting apparatus if the reception signal strength exceeds a threshold value, as a result of the comparison; and an output unit configured to output the generated assistance information, wherein
the packet includes a first packet in which biological data is stored.

* * * * *